(12) United States Patent
Allmendinger

(10) Patent No.: US 6,978,655 B2
(45) Date of Patent: Dec. 27, 2005

(54) SYSTEM, APPARATUS, AND METHOD FOR MEASURING AN OXYGEN CONCENTRATION OF A GAS

(75) Inventor: Klaus K. Allmendinger, San Juan Capistrano, CA (US)

(73) Assignee: Innovate! Technology, Inc., Irvine, CA (US)

( * ) Notice: Subject to any disclaimer, the term of this patent is extended or adjusted under 35 U.S.C. 154(b) by 40 days.

(21) Appl. No.: 10/699,182

(22) Filed: Nov. 1, 2003

(65) Prior Publication Data

US 2004/0149008 A1  Aug. 5, 2004

Related U.S. Application Data

(60) Provisional application No. 60/443,628, filed on Jan. 30, 2003.

(51) Int. Cl.[7] ......................... G01N 27/02; G01R 27/02
(52) U.S. Cl. .................................. 73/23.31; 73/31.05
(58) Field of Search ............................. 73/23.31, 31.05

(56) References Cited

U.S. PATENT DOCUMENTS

| 6,192,874 B1 | 2/2001 | Dekoninck et al. |
| 6,301,951 B1 | 10/2001 | Lenfers et al. |

FOREIGN PATENT DOCUMENTS

| DE | 19636226 A | 3/1998 |
| DE | 19800027 A | 7/1999 |
| EP | 0924514 A | 6/1999 |
| JP | 61118653 A | 6/1986 |
| JP | 63075553 A | 4/1988 |

*Primary Examiner*—Daniel S. Larkin
(74) *Attorney, Agent, or Firm*—Gavrilovich, Dodd & Lindsey, LLP

(57) ABSTRACT

An apparatus, system and method maximizes efficiency and accuracy of measuring an oxygen concentration of a measured gas by varying a flow of oxygen ions within a measuring cell (202) in accordance with an output signal of an oxygen sensor cell (206). The pump current (208) through a pump cell (204) is switched between a constant positive current and a constant negative current when upper and lower thresholds of the output signal are reached. The pulse width ratio of the square wave produced by the varying current is compared to a pulse width ratio function derived from a calibration procedure to determine the oxygen concentration of the measured gas.

41 Claims, 9 Drawing Sheets

*Fig. 1*   *(PRIOR ART)*

SYSTEM, APPARATUS, AND METHOD FOR MEASURING AN OXYGEN CONCENTRATION OF A GAS

RELATED APPLICATIONS

This application claims the benefit of priority of U.S. Provisional Application Ser. No. 60/443,628 filed on Jan. 30, 2003, entitled "System, Apparatus, And Method For Measuring An Oxygen Concentration Of A Gas" and which is incorporated in its entirety herein.

BACKGROUND OF THE INVENTION

The invention relates in general to oxygen sensors and more specifically to an apparatus, system and method for monitoring an oxygen concentration of a gas.

Oxygen sensors are used to measure the concentration of oxygen in a measured gas. Many conventional combustion engines utilize oxygen sensors for determining the air to fuel mixture of the exhaust of the combustion engine. Conventional internal combustion engines typically incorporate electronic fueling control using computing devices such as Electronic Control Units (ECU) that meter fuel into the engine intake depending on engine intake airflow. Typically, the volume of fuel is regulated such that emissions are minimized and all of the fuel is completely burned. The theoretical ratio of air to fuel for complete combustion is 14.7 by weight for gasoline, called the stoichiometric ratio. Theoretically, all available fuel combines with all the intake air at the stoichiometric ratio. The unit Lambda ($\lambda$) is often used to represent the quotient of actual air to fuel ratio over the region near the stoichiometric ratio. Conventional electronic fueling systems typically include an oxygen sensor in the exhaust that measures the oxygen concentration of the exhaust. These oxygen sensors act as fuel cells that create an output voltage by combining unburned hydrocarbons in the exhaust with atmospheric oxygen. This results in a lambda/output transfer curve where a $\lambda$ of 1.0 corresponds to an output voltage of 0.45V. Using the oxygen sensor, the fueling control system regulates the fueling such that the resulting lambda is 1.0 at medium load conditions using a feedback loop. The transfer curve of a typical oxygen sensor is very steep where $\lambda$ is equal to 1.0, however, and significant variations in output voltage occurs for slight variations in $\lambda$. Accordingly, the measured voltage cannot be used to measure other $\lambda$ values. At high load conditions, a typical internal combustion engine produces maximum power at lambda values<one (0.75 to 0.85). Conventional ECU systems operate in an 'open loop' mode under these conditions where the volume of injected fuel is derived solely from pre-stored maps that relate intake air mass to fuel mass without feedback. Because engine aging and production variations change the actual air fuel ratio of the engine, these pre-stored conditions are not always correct for the particular engine. As a result, conventional systems are limited in that severe inefficiencies can occur at high load conditions.

Some recent developments in engine technology have resulted in 'lean-burn' systems that operate at lambda ratios greater than 1 (up to 1.1) to minimize fuel consumption and further minimize emissions using special catalysators. Because ordinary lambda sensors are not usable in these lambda regimens, a 'wide-band' or Universal Exhaust Gas Oxygen (UEGO) sensor has been developed. UEGO sensors combine a small measurement chamber having an orifice open to the exhaust stream, a standard oxygen sensor (Nernst cell), and a pump cell. The pump cell is a solid-state device of porous ceramic that allows oxygen to move between the atmosphere and the measurement chamber. The direction and magnitude of the current through the pump cell (often referred to as the pump current) determines the direction and flow rate of oxygen ions. In conventional systems, an active feedback loop is incorporated such that the voltage at the oxygen sensor portion of the device is held at the stoichiometric voltage. The pump current can then be used to determine the $\lambda$ value over a wide range of ratios up to the ratio for free air.

FIG. 1 is graphical illustration of a typical relationship between the pump current and Lambda ($\lambda$). As shown in FIG. 1, the resulting curve of pump current vs. lambda value ($\lambda$) is non-linear. Although the curve shape does not vary, manufacturing tolerances in the sensors result in different magnitudes of pump current vs. lambda ($\lambda$) (i.e. the curve shifts). Attempts to compensate for the variations include incorporating a calibration resistor in the connector to the measuring cell sensor. Unfortunately, this attempted solution does not address all of the variations. Barometric air pressure and exhaust pressure also influence the lambda/pump current relationship. Accordingly, the outputs of theses sensors are not accurate. It is therefore desirable to have a measurement method for oxygen sensors that is self-calibrating and self-compensating for all the above variations.

The pump current vs. lambda curve is also highly temperature dependent. Typical UEGOs contain a heater element that maintains the sensor at the desired operating temperature. The temperature coefficient of the heater element is the quotient of change in resistance ($\Delta R$) to the change in temperature ($\Delta T$). Conventional techniques use the positive temperature coefficient of the heater element to regulate input by operating the element at a constant voltage. Because the temperature coefficient, $\Delta R/\Delta T$, is fairly small at the operating temperature, the resulting temperature regulation is not very precise. Depending on the sensor, the pump cell impedance, the Nernst cell impedance, or both have a much bigger temperature coefficient, $\Delta R/\Delta T$, and would, therefore, allow more precise temperature control. It would be more advantageous to control the temperature of the pump cell. Unfortunately, at lambda values near 1, the pump current is very small or equal to zero and the pump cell impedance can not be accurately measured on a low current. The Nernst cell is typically physically bonded to the pump cell and, therefore, the temperature of the Nernst cell and the pump cell differ by a small amount. In order to measure the Nernst cell impedance, a known fixed current or known fixed voltage have to be impressed on the Nernst cell and the resulting voltage or current then measured. Alternatively, a small alternating current (AC) voltage or current can be impressed on the Nernst cell and the resulting AC impedance measured. The first method requires stopping the lambda measurement for a period of time and also requires impressing the reverse charge on the Nernst cell to speed up recovery. The second method does not interfere with the measurement but requires low pass filters to remove the AC voltage or current from the measured signal. The filters also remove the higher signal frequencies which results in an inability to detect short transient responses. Both methods measure the temperature of the Nernst cell, not the pump cell. During operation, a temperature gradient between the pump cell and the Nernst cell may occur and some temperature control errors may result. Therefore there is a need for precise pump cell temperature control while measuring lambda without resorting to complicated circuitry to remove measurement artifacts.

Further, conventional fuel metering techniques result in significant pollution during the warm up period of the oxygen sensor. In conventional systems where UEGO sensors are used, a precise operating temperature must be attained before the UEGO output value is reliable. This increases the time the fuel injection systems runs in 'open loop' without knowledge of actual air-fuel ratio. As a result, the time the engine creates uncontrolled warm-up pollution is dependent on the sensor warm-up time. Therefore, there also exists a need for an apparatus, system and method for measuring an oxygen concentration which minimizes the time before a reliable value is produced by the sensor.

DETAILED DESCRIPTION OF THE PREFERRED EMBODIMENTS

As explained above, conventional oxygen sensor systems are limited in several ways. These limitations are overcome in the exemplary embodiment which provides an efficient, low cost, accurate method for measuring an oxygen concentration of gas. An oxygen concentration of a gas is measured by varying a pump current through an oxygen measuring cell based on an output of the measuring cell and observing the pulse width ratio of the resulting square wave representing the pump current. Further, in some circumstances, the method described herein allows the sensor to be used earlier in the warm-up period because the measurement method allows the application of a correction factor that compensates for the fact that the sensor has not yet achieved its desired operating temperature. Also, the exemplary embodiment described herein allows precise pump cell temperature control while measuring lambda without resorting to complicated circuitry to remove measurement artifacts.

Figure 1:
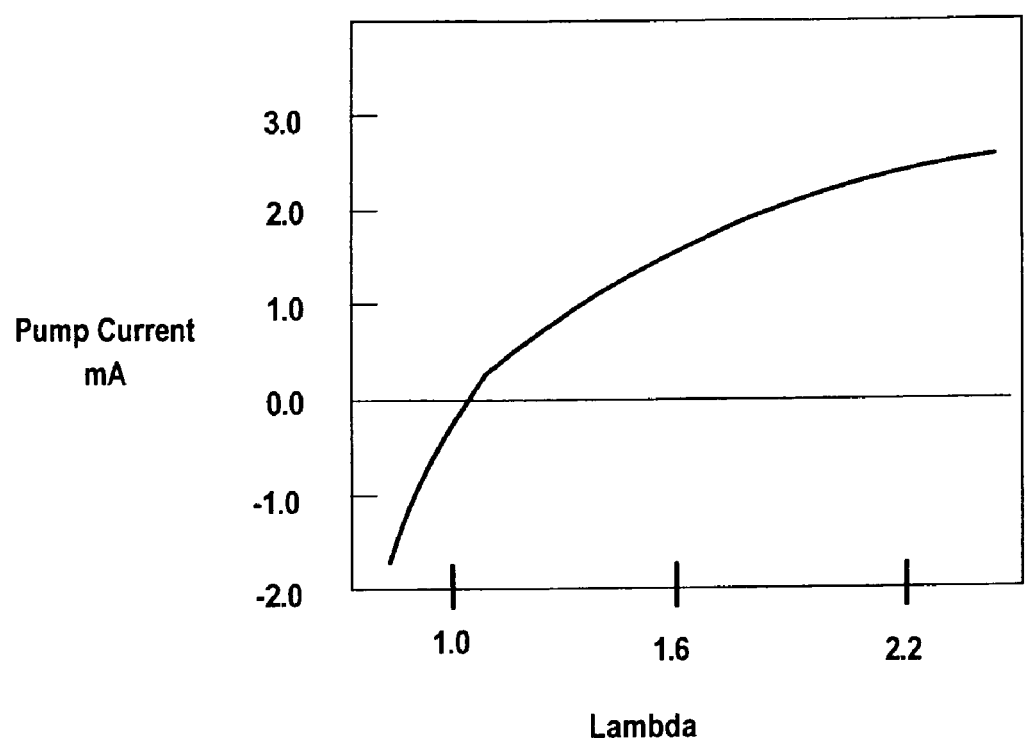
FIG. 1 is graphical representation of a relationship between pump current and an air to fuel ratio, Lambda (λ), for a typical Universal Exhaust Gas Oxygen (UEGO) sensor.
Figure 2:
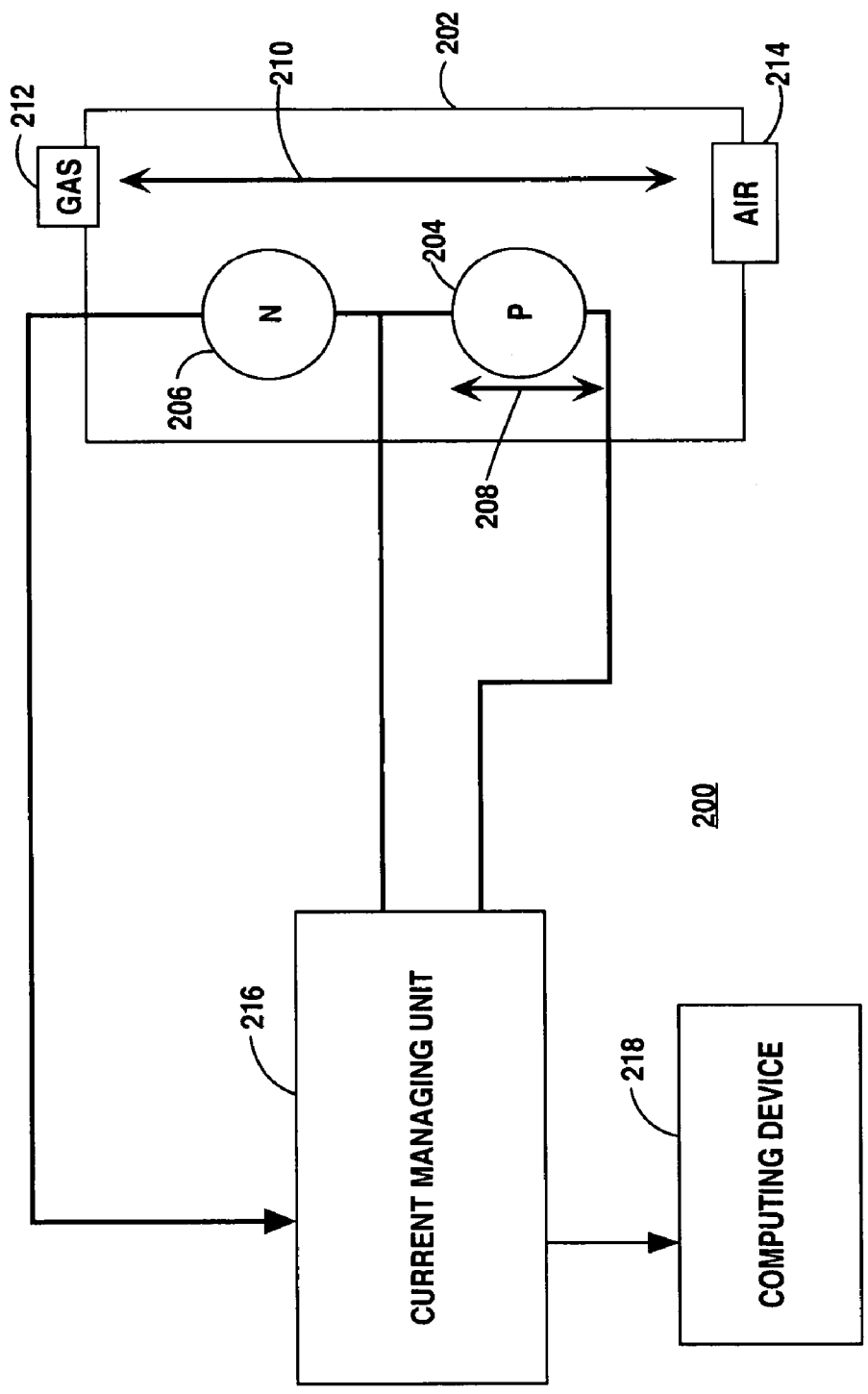
FIG. 2 is a block diagram of the oxygen monitoring device in accordance with an exemplary embodiment of the invention.

FIG. 2 is a block diagram of the oxygen monitoring device 200 in accordance with an exemplary embodiment of the invention. The oxygen monitoring device 200 may be implemented using any combination of hardware, software and firmware. Various functions and operations of the functional blocks described herein may be implemented in any number of devices, circuits or elements. Any of the functional blocks may be integrated in a single device and the functions of the blocks may be distributed over several devices, circuits and elements.

A measuring cell 202 includes at least a pump cell 204 and an oxygen sensor cell 206 where a magnitude and direction of a pump current 208 through the pump cell 204 is correlated to a flow of oxygen ions 210 within the measuring cell 202. A measuring opening 212 of the measuring cell 202 is positioned to receive a measured gas while an air opening 214 faces ambient air. The oxygen sensor cell 206 provides an output signal based on the number of oxygen ions within the measuring cell 202. In response to the output signal, a current managing unit 216 varies the pump current between two constant current levels. A first pump current is maintained by the current managing unit 216 until the output signal reaches a first threshold. When the first threshold is reached, the current managing unit 216 directs the pump current 208 in the opposite direction until the output signal reaches a second threshold level. A computing device 218 monitors the current fluctuation to determine an oxygen concentration of the measured gas. A suitable application of the oxygen monitoring device 200 includes monitoring exhaust gas from a combustion engine to adjust an air-fuel mixture. The oxygen monitoring device, method and system may be implemented as part of any of several types of applications and systems. As discussed below, for example, the oxygen monitoring device may be implemented as a hand-held diagnostic device, as an original equipment manufacturer (OEM) device within a vehicle or as an aftermarket device for permanent installation in a vehicle. In addition, the oxygen measuring device 200 may be used to measure the oxygen concentration of exhaled gases from a living being to determine the number of calories that are being expended.

In the exemplary embodiment, the oxygen sensor cell 206 is a Nernst cell (206) that is positioned adjacent to a pump cell 204 in accordance with known techniques. Other types of oxygen sensor cells 206 may be used, however. It is understood by those skilled in the art that although the following description refers to a Nernst cell (206), the invention may be implemented with other oxygen sensor cells 206 capable of providing an output signal based on the oxygen level in a measured gas. After a calibration procedure is performed in accordance with the procedure described below, the current managing unit 216 varies the current 208 through the pump cell 204 between a constant positive current (Ip) and a constant negative current (−Ip) based on the output signal of the Nernst cell (206). When a negative current (−Ip) flows through the pump cell 204, ambient air is received through the air opening 214 into the measuring cell 202 through the pump circuit which results in an increase of the concentration of oxygen within the measuring cell 202. At a high concentration of oxygen within the measuring cell 202, the Nernst cell (206) provides a low voltage signal output. When an output signal lower threshold is reached, the current managing unit 216, directs a positive current (Ip) through the pump cell 204. When a positive current (Ip) flows through the pump cell 204, the oxygen ions in the measuring cell 202 flow out to ambient air. Any unburned carbons or fuel within the measuring cell 202 combine with any remaining oxygen. As a result, the mixture of air and unburned carbons within the measuring cell 202 decreases in oxygen concentration and increases in fuel concentration. The output signal increases through the transition point where no unburned fuel and no excess oxygen is present in the measuring cell 202. At this transition point, lambda is equal to 1.0 and the Nernst cell (206) provides an output signal of approximately 450 mV. As the positive pump current 208 (Ip) continues to flow, oxygen ions continue to flow out of the air opening 214. As a result, the concentration of oxygen continues to decrease and the concentration of fuel increases in the measuring cell 202. The output signal continues to increase until an upper threshold is reached. In response to detecting that the upper threshold has been reached, the current managing unit 216 changes the direction of the pump current 208. In the exemplary embodiment, the upper threshold is 455 mV and the lower threshold is 445 mV. Other thresholds, however, can be used where some suitable values include values providing a range that includes the output signal for gas of ambient air and which maintain the Nernst cell (206) within a relatively linear potion of the lambda to voltage relationship. For example, another suitable pair of values includes 440 mV and 460 mV.

A square wave is formed between the positive and negative current levels. The duration of the pump current 208 at positive flow (Ip) and negative flow (-Ip) depends on the composition of the measured gas. Accordingly, the computing device 218 compares the pulse width ratio ($PWM_{RATIO}$) of the resulting square wave to a known pulse width ratio function to determine the oxygen concentration of the measured gas.

Figure 3:
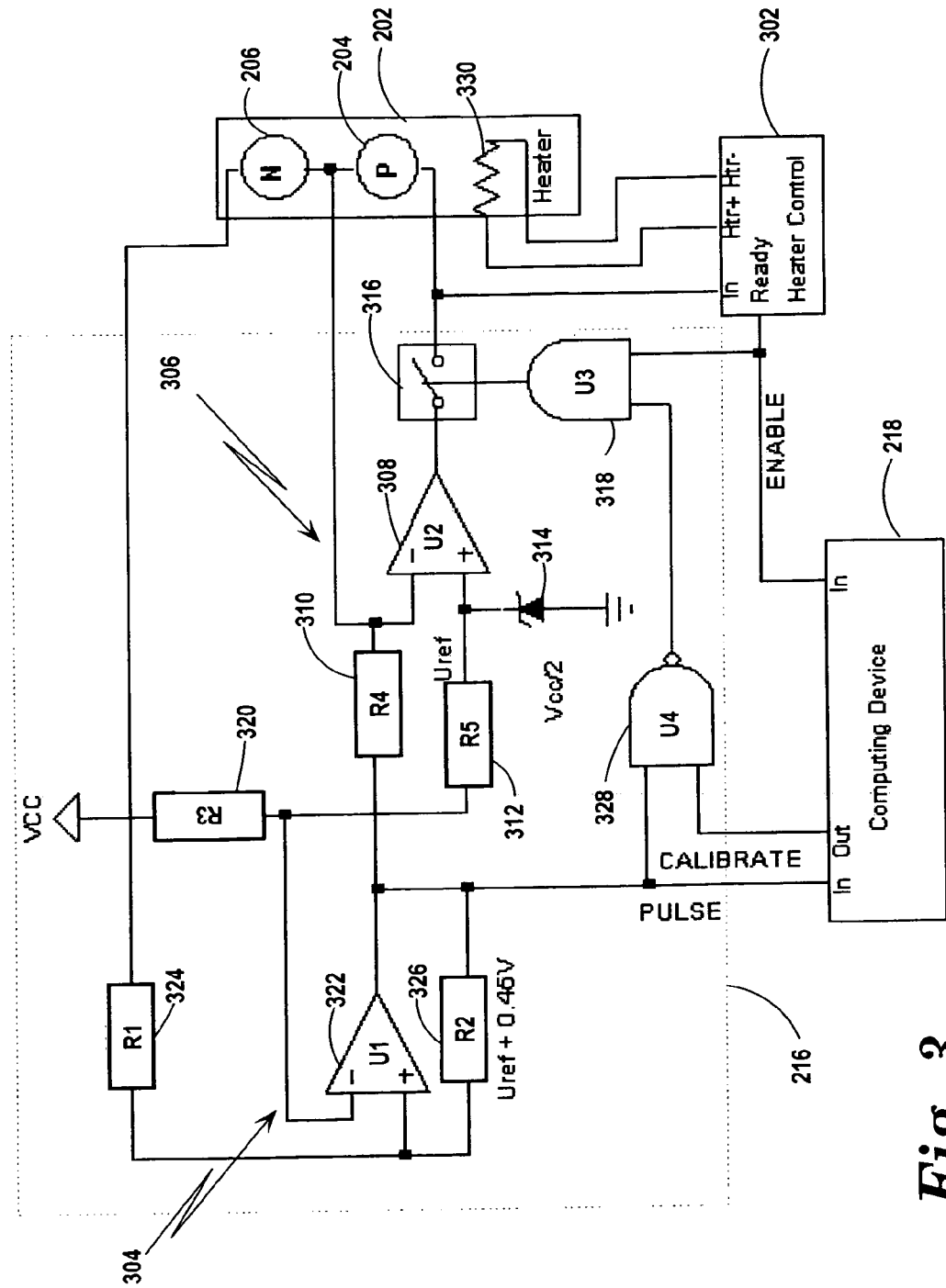
FIG. 3 is a schematic representation of the oxygen monitoring device where the current managing unit is implemented using an analog comparator circuit and an inverting amplifier circuit in accordance with the exemplary embodiment of the invention.

FIG. 3 is a schematic representation of the oxygen monitoring device 200 where the current managing unit 216 is implemented using an analog comparator circuit 304 and an inverting amplifier circuit 306 in accordance with the exemplary embodiment of the invention. The current managing device 216 may be implemented using any combination and arrangement of hardware, software and firmware. In the exemplary embodiment, the current managing device 216 includes several hardware components including resistors, operational amplifiers, analog switches, Zener diodes, logic gates and other circuits. Those skilled in the art will recognize the various substitutions that can be made for one or more circuits or circuit elements by applying the teachings herein in accordance with known techniques. Further, the operating values may differ depending on the particular implementation of the current managing device 216.

The inverting amplifier circuit 306 at least includes an operational amplifier ($U_2$) 308, an inverting input resistor ($R_4$) 310, and a non-inverting input resistor ($R_5$) 312. The voltage at the non-inverting input of the operational amplifier ($U_2$) 308 is maintained at voltage of $U_{REF}$ by a Zener diode 314. $U_{REF}$ is equal to Vcc/2 which is approximately 2.5 volts in the exemplary embodiment. The pump cell 204 in the measuring cell 202 is connected through an analog switch 316 between the output of the operational amplifier ($U_2$) 308 and the inverting input of the operational amplifier ($U_2$). The operational amplifier ($U_2$) 308, inverting input resistor ($R_4$) 310 and the pump cell 204 impedance ($R_{pump}$) form the inverting amplifier 306 with a gain of $-R_{pump}/R_4$. The output of the operational amplifier ($U_2$) 308 is connected to the analog switch 316 that connects the output of the operational amplifier 308 to the pump cell 204 in response to the output level of an AND gate ($U_3$) 318. Since the AND gate 318 provides an active "high" output when the heater control unit 302 presents a "high" enable signal, the analog switch 316 prevents current from flowing through measuring cell 202 during warm up. Further, as explained below, during the calibrate procedure, the analog switch 316 is opened during the negative pump current 208 cycle resulting in a pump current 208 that alternates between a positive pump current (IP) and zero.

The inverting input of the operational amplifier ($U_2$) 308 is connected to the output of the analog comparator circuit 304 through the inverting input resistor ($R_4$) 310. The non-inverting input resistor ($R_5$) 312, a supply resistor ($R_3$) 320 and the Zener diode 314 form a voltage divider and present a reference voltage of (Vcc/2+0.45V) to the inverting input of an operational amplifier ($U_1$) 322 of the analog comparator circuit 304. In the exemplary embodiment, the reference voltage is 2.95 Volts since Vcc is 5 Volts. The positive input of the operational amplifier 322 is connected to the output of the Nernst cell (206) through a sensing resistor ($R_1$) 324. A feedback resistor ($R_2$) 326 provides a voltage equal to $U_{REF}$+0.45V to the positive input of the operational amplifier 322. Therefore, the operational amplifier ($U_1$) 322, the resistor ($R_1$) 324, and the feedback resistor ($R_2$) 326 form the analog comparator circuit 304 operating with a hysteresis voltage of approximately 10 mV.

The analog comparator circuit 304, the inverting amplifier circuit 306 and the measuring cell 202 form an oscillator with a variable pulse width modulation (PWM) ratio and a frequency that is dependent on the response time of the measuring cell 202. The pump current 208 alternates between +Vcc/(2*R4) and -Vcc/(2*R4). The computing device 218 measures the times the output of U2 spends above ($t_1$) and below Vcc/2 ($t_2$) and from that calculates the $PWM_{RATIO}$ and λ according to the function described below. Lambda (λ) is calculated at every transition of the output of the comparator in the exemplary embodiment. The Nernst cell (206) provides an output signal approximately between 0.1 V and 0.7 V and the resulting (λ) measurement frequency is about 7 octaves higher than the 3 dB point of the response frequency of the oxygen sensor cell 206. Accordingly, the oxygen sensor cell 206 response frequency is well above the Nyquist frequency in the exemplary embodiment.

In the exemplary embodiment, the heater control unit 302 increases the temperature of the measuring cell 202 using a sensor specific method and ramp-up schedule. After the measuring cell 202 has achieved its operating temperature, the "Ready" output of the heater control unit 302 goes active providing a high ENABLE signal to the AND gate ($U_3$) which closes the analog switch 304. The enable signal is also connected to an input of the computing device 218 and indicates to the computing device 218 that the measuring cell 202 is ready for operation. The heater control unit 302 then maintains a constant predetermined voltage over the heater element or uses other (sensor specific) methods for temperature regulation. In the exemplary embodiment, the pump cell impedance is measured when the heater element 330 impedance is at the minimum value. The pump cell impedance is maintained at the measured value by continually monitoring the pump cell impedance and adjusting the temperature with the heater element 330.

As described below with reference to FIG. 6, the computing device 218 stores values in non-volatile memory corresponding to the PWM ratio at the stoichiometric ratio ($PWM_{ST}$) and the pulse width ratio for air ($PWM_{AIR}$). In the exemplary method described below with reference to FIGS. 4–8, a nominal lambda value having an error on the order of +/−5% is calculated based on the calibration values and the measured $PWM_{RATIO}$. Because $PWM_{ST}$ is dependent on the characteristics and age of the sensor much more than on environmental conditions, the calibration process does not need to be performed very often in most circumstances.

Based on these teachings, those skilled in the art will recognize the various components, devices, and circuits elements that can be used in the measuring device. An example of suitable device that can be used for the operational amplifiers 308, 322 include the TLV2463 operational amplifier available from the Texas Instruments company. Values for the inverting resistor ($R_4$) 310 and the non-inverting ($R_5$) resistor 312 are on the order of a few hundred ohms. An example of suitable computing device 218 includes an 850 Family RISC 8-Bit Microcontroller. In some circumstances, some or all of the functional blocks described above may be implemented as an application specific integrated circuit (ASIC). For example, heater control and current managing unit 216 and computing device 218 can be easily integrated into a mixed signal ASIC with very few external parts.

Figure 4:
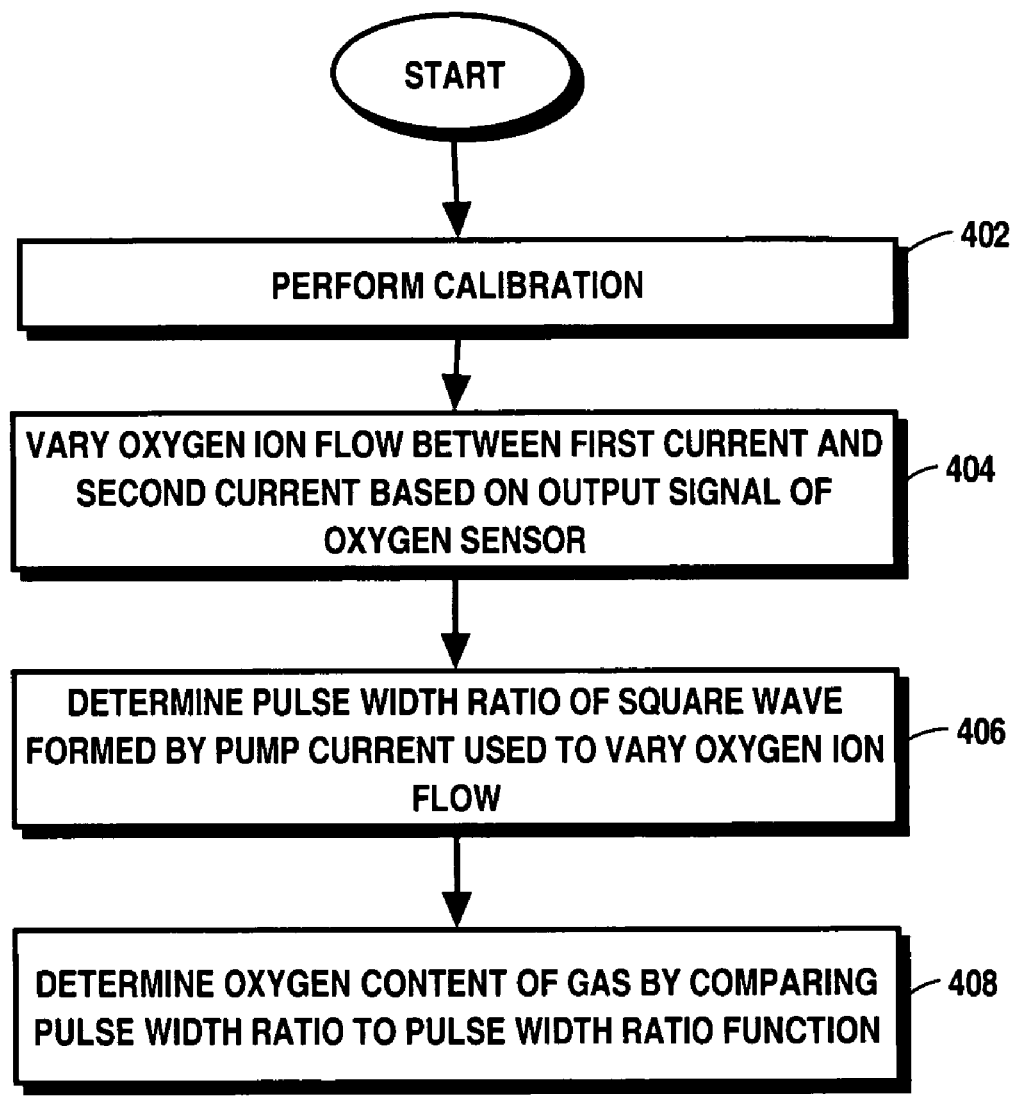
FIG. 4 is a flow chart of a method of measuring an oxygen concentration of a gas in accordance with the exemplary embodiment of the invention.

FIG. 4 is a flow chart of a method of measuring an oxygen concentration of a gas in accordance with the exemplary embodiment of the invention. The method may be performed with any combination of hardware, software or firmware. In the exemplary embodiment, the method is performed in the oxygen measuring device 200.

At step 402, a calibration procedure is performed. The calibration procedure obtains the calibration values for initializing the oxygen measuring device and may include values related to the characteristics of the particular measuring cell 202 or related to environmental conditions. As explained below with reference to FIG. 6, in the exemplary embodiment, values are obtained for maintaining the pump cell 204 impedance, for establishing the pulse width ratio function for calculating lambda, and for adjusting the lambda value when the PWM ratio for a stoichiometric ratio ($PWM_{ST}$) is not zero. Other calibration values may include parameters related to the frequency of a square wave of the pump current 208 reflecting oxygen sensor characteristics.

At step 404, the oxygen ion flow is varied between a first pump current and a second pump current based on the output signal of the oxygen sensor cell 206. In the exemplary embodiment, the ion flow is varied by alternating the pump current 208 between a positive constant current (IP+) and a negative constant current (IP−). The analog switch 316 remains closed during the measurement procedure.

At step 406, the pulse width ratio ($PWM_{RATIO}$) of the square wave formed by the pump current 208 is determined by the computing device 218. In the exemplary embodiment, the pulse widths ($t_1$ and $t_2$) of the square wave formed by the varying pump current 208 are measured using a crystal clock in the computing device 218. Although individual values of a single pulse can be measured and stored, the duration of the pulses resulting form the varying current are averaged over a time period.

At step 408, the pulse width ratio ($PWM_{RATIO}$) is compared to the pulse width ratio function to determine the oxygen concentration of the measured gas. In the exemplary embodiment, the computing device 218 applies the measured values to equations that utilize the calibrated values.

Figure 5:
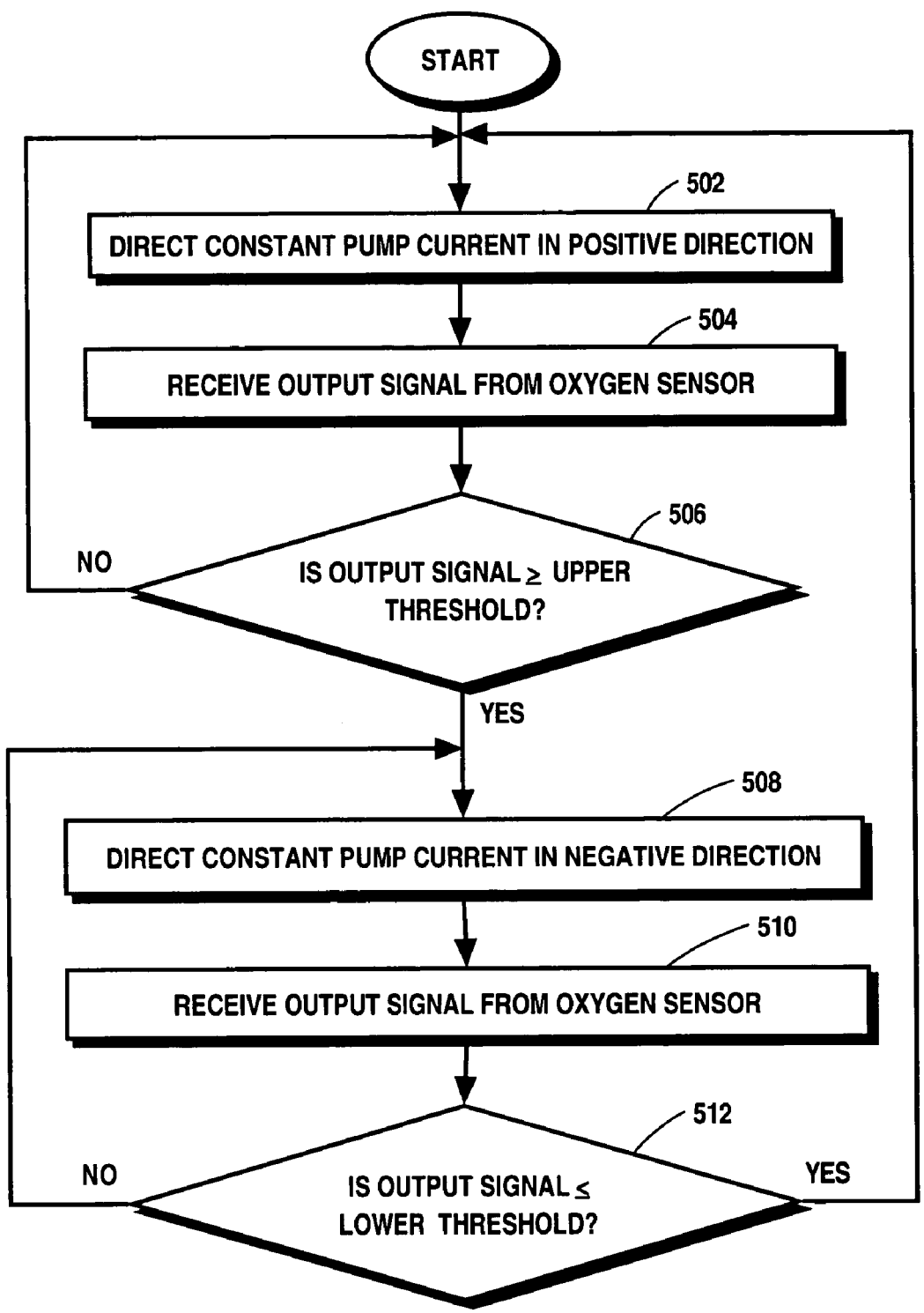
FIG. 5 is a flow chart of a method of varying the oxygen ion flow within the measuring cell in accordance with the exemplary embodiment.

FIG. 5 is a flow chart of a method of varying the oxygen ion flow within the measuring cell 202 in accordance with the exemplary embodiment. The flow chart of FIG. 5, therefore, illustrates an exemplary method of performing step 404 of FIG. 4.

At step 502, the pump current 208 is directed in a positive direction through the pump cell 204 at a constant magnitude. In the exemplary oxygen monitoring device 200 described with reference to FIG. 3, the analog switch 316 remains closed as positive voltage is applied across the pump cell 204. The positive voltage is maintained until the analog comparator circuit 304 triggers the inverting amplifier 308 to applying a negative voltage across the pump cell 204.

At step 504, the output signal from the oxygen sensor cell 206 is received. In the exemplary oxygen monitoring device 200, the output of the oxygen sensor cell 206 is received through the resistor ($R_1$) 324 at the positive input of the operational amplifier 322 of the analog comparator circuit 304.

At step 506, it is determined whether the output signal is greater than or equal to the upper threshold. If the upper threshold has not been reached, the method returns to step 502 where the constant positive pump current is directed through the pump cell 204. If the upper threshold has been reached, the method continues at step 508 where the current is reversed and a constant pump current 208 is directed in the negative direction. As discussed above with reference to FIG. 3, in the exemplary embodiment, the current managing device 216 includes an analog comparator circuit 304 and an inverting amplifier circuit 306 to provide the constant current until the thresholds are reached. The analog comparator circuit 304 triggers the reverse of the pump current 208 in response to the detection that the thresholds have been reached. Therefore, the positive pump current (IP+) is maintained until the output of the oxygen sensor cell 206 reaches an upper threshold that causes the output of the analog comparator circuit 304 to switch to a high output changing the output of the inverting amplifier circuit 306.

At step 508, the pump current 208 is directed in a negative direction. In response to the reversed voltage output of the inverting amplifier circuit 306 the pump current 208 reverses direction and becomes negative (−Ip).

At step 510, the current managing unit 216 receives the output signal from the oxygen sensor cell 206. In the exemplary oxygen monitoring device 200, the output of the oxygen sensor cell 206 is received through the resistor ($R_1$) 324 at the positive input of the operational amplifier 322 of the analog comparator circuit 304.

At step 512, it is determined if the output signal is less than or equal to the lower threshold. Of the lower threshold has not yet been reached, the method returns to step 508 where the current managing unit 218 continues to direct the pump current 208 in a negative direction through the pump cell 204. Otherwise, the procedure returns to step 502, where the current is reversed to the positive direction. Accordingly, in the exemplary embodiment, the current managing device 216 varies the current between 0.445 volts and 455 volts based on the output of the oxygen sensor cell 206. As the pump current 208 is varied, characteristics of the resulting square wave are measured and stored.

In the exemplary embodiment, the computing device 218 monitors the time periods ($t_1$ and $t_2$) and if either of the time periods exceeds a operating threshold, the computing device 218 overwrites the ENABLE signal and disconnects the pump cell 204 to prevent damage to the sensor. A diagnostic procedure is performed to determine the fault condition.

Figure 6:
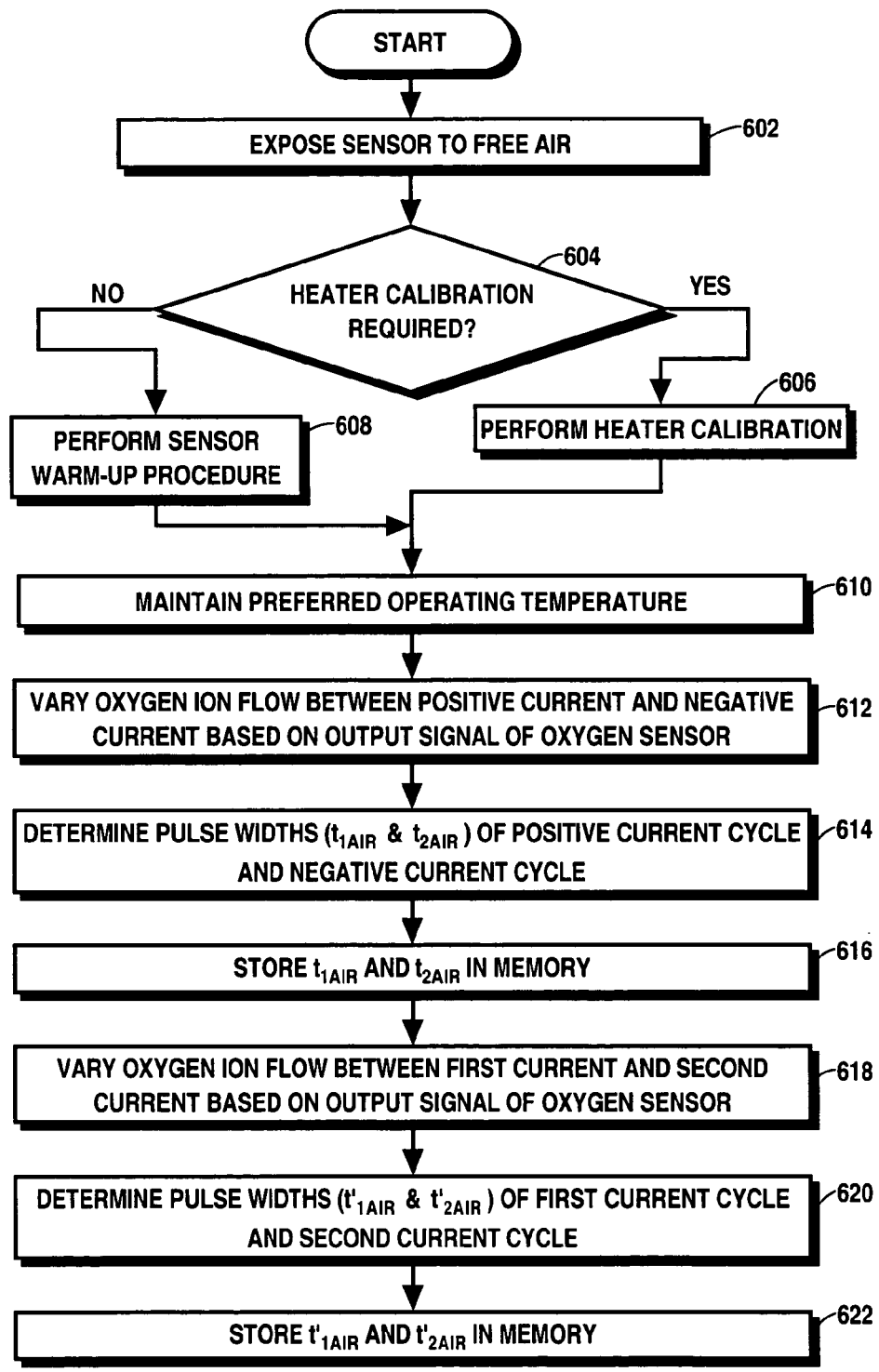
FIG. 6 is a flow chart of a method of calibrating an oxygen measuring device in accordance with the exemplary embodiment.

FIG. 6 is a flow chart of an exemplary method of calibrating the oxygen monitoring device 200. The method described with reference to FIG. 6 provides and exemplary method of performing the calibration step 402 of FIG. 4. The oxygen monitoring device 200 may be calibrated in any number of ways and the particular calibration method used may depend on a variety of factors such as the characteristics of the particular sensor 202 and the data that will be collected using the oxygen monitoring device 200. In the exemplary embodiment, the calibration procedure includes calibrating the heater control unit 302 and determining the pulse widths of the varying pump current 208 when the oxygen sensor cell 206 is exposed to free air.

At step 602, the oxygen sensor cell 206 is exposed to free air. In the exemplary embodiment, the measuring cell 202 is placed in an area where exposure to exhaust gases or other air borne impurities is minimized. In some circumstances where the oxygen measuring device 200 is operating in a functioning vehicle, the computing unit determines that the engine is in a coast down mode when the resulting lambda value is above the lean burn limit for gasoline and not changing over some period of time. When it is determined that the vehicle is in a coast down mode, the computing device 218 performs the calibration procedure. If the computing device 218 is the ECU itself, the coast down condition is already known and the ECU, after the predetermined purge time of the exhaust system, performs the calibration procedure for free air.

At step 604, it is determined whether the heater control unit 302 should be calibrated. In the exemplary embodiment, the heater control unit 302 is calibrated during the powering up sequence. Examples of other suitable situations that require the heater calibration procedure to be performed include the replacement or reconnection of the measuring cell 202 and the detection of certain measurement errors. If heater calibration is required, the procedure continues at step 606. Otherwise, the proceeds directly to step 608.

At step 606, the heater control unit 302 is calibrated. In the exemplary embodiment, a preferred heater impedance and a preferred pump cell impedance corresponding to a preferred operating temperature of the Nernst cell 206 are stored in memory. As discussed with reference to FIG. 8, the Nernst cell impedance is maintained at a target Nernst cell impedance for a suitable time period before the preferred heater impedance and the preferred pump cell impedance are measured and recorded.

At step 608, a sensor warm-up procedure is performed. In the exemplary monitoring device described with reference to FIG. 3, the analog switch 316 is initially opened during the sensor warm-up procedure. In accordance with the appropriate heating timetable, power is applied to the heater element 330 to increase the temperature. The heater control unit 302 monitors the current and voltage across the heating element 330 and determines the impedance of the heater element 330. The heater impedance is compared to the preferred heater impedance that was measured and stored during the heater calibration procedure. When the heater control unit detects that the heater impedance is equal to the preferred heater impedance, the heater control unit 302 determines that the minimum operating temperature of the oxygen sensor cell 206 has been reached. In response to a determination that the desired operating temperature is reached, the heater control unit 302 presents a "high" enable signal at the "Ready" output. The AND gate (U3) 318 closes the analog switch 316 when the ENABLE signal goes "high".

At step 610, the preferred operating temperature of the Nernst cell is maintained. The preferred operating temperature is maintained during the remainder of the oxygen sensor calibration procedure as well as during operation of the oxygen monitoring device 200. In the exemplary embodiment, the pump cell 204 impedance $R_{PUMP}$ is constantly monitored during operation and the heater control unit 302 is controlled to maintain a constant, or nearly constant, preferred pump cell impedance. The preferred pump cell impedance is retrieved from memory where it was stored during the heater calibration procedure. An example of a suitable method of controlling the heater control unit 302 includes using pulse width modulation to increase or decrease the amount of power dissipated by the heater element 330.

When the oxygen measuring device 200 is in an oscillating mode and the current is varied, the voltage at the pump cell 204 (output of $U_2$) is determined by Vcc, $R_{PUMP}$, the resistor $R_4$ 310, and the back-EMF of the pump cell 204. The output of the operational amplifier ($U_1$) 322 of the analog comparator circuit 304 switches between 0V and Vcc. The heater control unit 302 samples the output of the operational amplifier ($U_2$) 308 before and after each transition of the output of the operational amplifier ($U_1$) 322. The absolute value of the difference between the voltage measured before and after each transition is $U_{DIFF}$. In some circumstances, the output of the operational amplifier ($U_2$) 308 is passed through a high pass filter (not shown) of sufficiently high cut-off frequency. The filter output is sampled immediately after the transition point and the absolute value of resulting output voltage is equal to $U_{DIFF}$.

The heater control unit 302 calculates the pump cell 204 impedance $R_{PUMP}$ in accordance with the following relationship:

$$R_{PUMP}=R_4(U_{DIFF}/Vcc) \quad (1)$$

In some circumstances, the Nernst cell (206) impedance ($R_N$) is monitored as an alternative or in addition to monitoring the pump cell 204 impedance. In order to monitor the Nernst cell (206) impedance, the output voltage signal of the Nernst cell (206) is passed through a high pass filter and amplifier (not shown). The resulting filtered and amplified signal is then sampled at the comparator transition point. The peak-peak voltage, $U_{NPP}$, is then calculated as the difference between the sample voltage at low-high and high-low transition.

The voltage $U_{NPP}$ follows the equation:

$$U_{NPP}=Vcc(R_1+2R_N)/R_2 \quad (2)$$

$U_{NPP}$, therefore, linearly follows the Nernst cell (206) impedance, $R_N$, and is a convenient measurement for the Nernst cell (206) impedance without the use of any filtering in the signal path to influence the measured lambda signal. The resistors, $R_1$ and $R_2$, are chosen such that the current through $R_N$ is small enough to not influence the function of the Nernst cell (206) and such that the $U_{NPP}$ at the Nernst operating temperature and impedance is approximately 10 mV.

At step 612, the oxygen ion flow 210 is varied between a positive current (Ip) and the negative current (-Ip) based on the output signal of the oxygen sensor cell 206. An example of suitable method of varying the current 208 is described above with reference to FIG. 5.

At step 614, the pulse width ratio for air ($PWM_{AIR}$) is determined. In the exemplary embodiment, the pulse widths ($t_{1AIR}$ and $t_{2AIR}$) are determined for the positive current cycle and the negative current cycle. The transition times of the square wave are timed by a crystal clock within the computing device 218 to measure the pulse widths. The values for the pulse widths are measure and averaged over a sufficient time period such as one second, for example, to calculate an average $PWM_{AIR}$.

If the pulse width ratio for air is calculated during a coast down condition, the computing device 218 determines when the condition is reached before measuring the pulse widths of the pump current 208. If the computing device 218 is an ECU in the system, the ECU detects the condition based on parameters directly available to the ECU such as throttle position and engine speed.

At step 616, $PWM_{AIR}$ is stored in memory. Various techniques may be used to store and retrieve calibration information. For example, the pulse widths ($t_{1AIR}$ and $t_{2AIR}$) may be stored directly into memory and used for calculating $PWM_{AIR}$ at a later time. Such a procedure may be desired where the frequency of the square wave is used to further compensate for pressure and temperature variations. By storing the pulse width timing, frequency information is stored in addition to the average pulse width ratio for air ($PWM_{AIR}$).

At step 618, the oxygen ion flow 210 is varied between a first current and second current based on the output signal of the oxygen sensor cell 206. In the exemplary embodiment, the current 208 is varied between (IP) and zero. In a manner similar to the method described above, the current 208 is varied from a first current to a second current except that a zero current is used in place of the negative current (IP-).

At step 620, the pulse width ratio for air when the second current is zero ($PWM'_{AIR}$) is determined. In the exemplary embodiment, the pulse widths ($t'_{1AIR}$ and $t'_{2AIR}$) are determined for the positive current cycle and the zero current cycle. The transition times of the square wave are timed by a crystal clock within the computing device 218 to measure the pulse widths. The values for the pulse widths are measure and averaged over a sufficient time period such as one second for example to calculate an average $PWM'_{AIR}$. To measure $PWM_{AIR}'$, the computing device 218 sets the signal CALIBRATE high. The NAND-Gate ($U_4$) 328 together with AND-Gate ($U_3$) 318 thus cause the analog switch 316 to switch on only during the high phase of the pump current 208. During the low phase, the analog switch 316 is off and no pump current can flow.

At step 622, $PWM'_{AIR}$ is stored in memory. Various techniques may be used to store and retrieve calibration information. For example, the pulse widths ($t'_{1AIR}$ and $t'_{2AIR}$) may be stored directly into memory and used for calculating $PWM'_{AIR}$ at a later time.

Other calibration procedures may be performed in some situations. Calibration procedures for pressure and temperature compensation, for example, may be performed by measuring and storing frequency information corresponding to the pump current 208 at certain calibration conditions.

Figure 7:
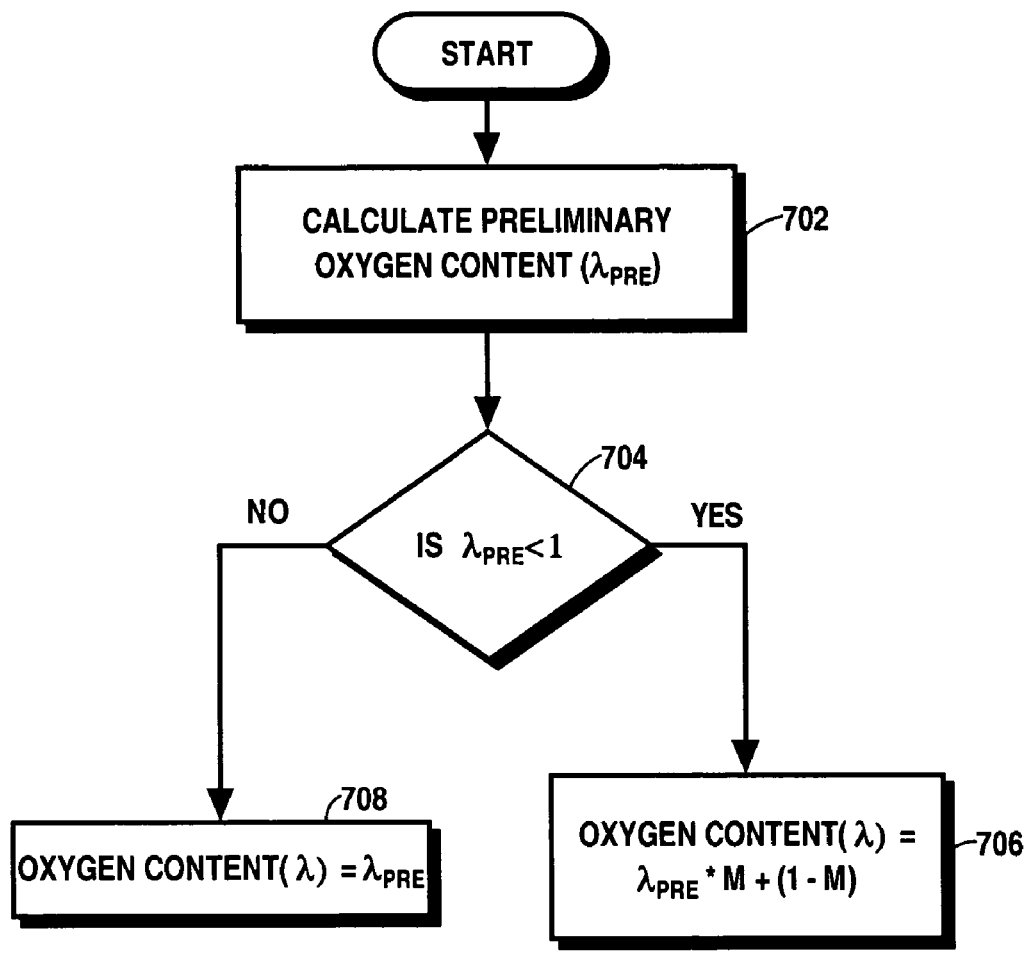
FIG. 7 is a flow chart of a method of determining the oxygen concentration of a gas by comparing the measured pulse width ratio ($PWM_{RATIO}$), to the pulse width ratio function in accordance with the exemplary embodiment of the invention.

FIG. 7 is a flow chart of a method of determining the oxygen concentration of a gas by comparing the measured pulse width ratio, $PWM_{RATIO}$, to the pulse width ratio function in accordance with the exemplary embodiment of the invention. The method described with reference to FIG. 7 is an exemplary method of performing step 408 of FIG. 4.

At step 702, a preliminary oxygen concentration, ($\lambda_{PRE}$) is calculated. In the exemplary embodiment, the preliminary oxygen concentration ($\lambda_{PRE}$) is determined by the following equation:

$$\lambda_{PRE} = P/(PWM_{AIR} - PWM_{RATIO}) \quad (3)$$

where $P = (1 + PWM'_{AIR})(1 - PWM_{AIR})/(1 - PWM'_{AIR})$ (4)

The computing device 218 retrieves from memory the values for $PWM_{AIR}$, $PWM_{RATIO}$, and $PWM'_{AIR}$ and applies the above equations to calculate the preliminary oxygen concentration, $\lambda_{PRE}$. As explained below, P is equal to $PWM_{AIR}$ where the pulse width ratio at the stoichiometric ratio ($PWM_{ST}$) is zero. Therefore, $\lambda_{PRE}$ is equal to $PWM_{AIR}/(PWM_{AIR} - PWM_{RATIO})$ where the $PWM_{ST}$ for the particular sensor is zero.

At step 704, it is determined whether $\lambda_{PRE}$ is less than one. If $\lambda_{PRE}$ is less than one, the procedure continues at step 706. Otherwise, the procedure continues at step 708, where the oxygen concentration ($\lambda$) of the gas is determined to be equal to the preliminary oxygen concentration, $\lambda_{PRE}$.

At step 706, the oxygen concentration ($\lambda$) of the gas is determined to be equal to the sum of the preliminary oxygen concentration ($\lambda_{PRE}$) multiplied by a calibration factor (M) and 1 minus the calibration factor ($\lambda = (\lambda_{PRE})*M + (1-M)$). In the exemplary embodiment, a calibration factor, M, for the brand and model of the particular measuring cell 202 is derived through statistical analysis of the measuring cell's 202 performance when exposed to a gas with a known oxygen concentration. In some circumstances, a calibration factor for each of several measuring cells is stored in memory and applied to the particular model that is connected within the oxygen measuring device 200. An example of typical value of M is 0.71428.

Figure 8:
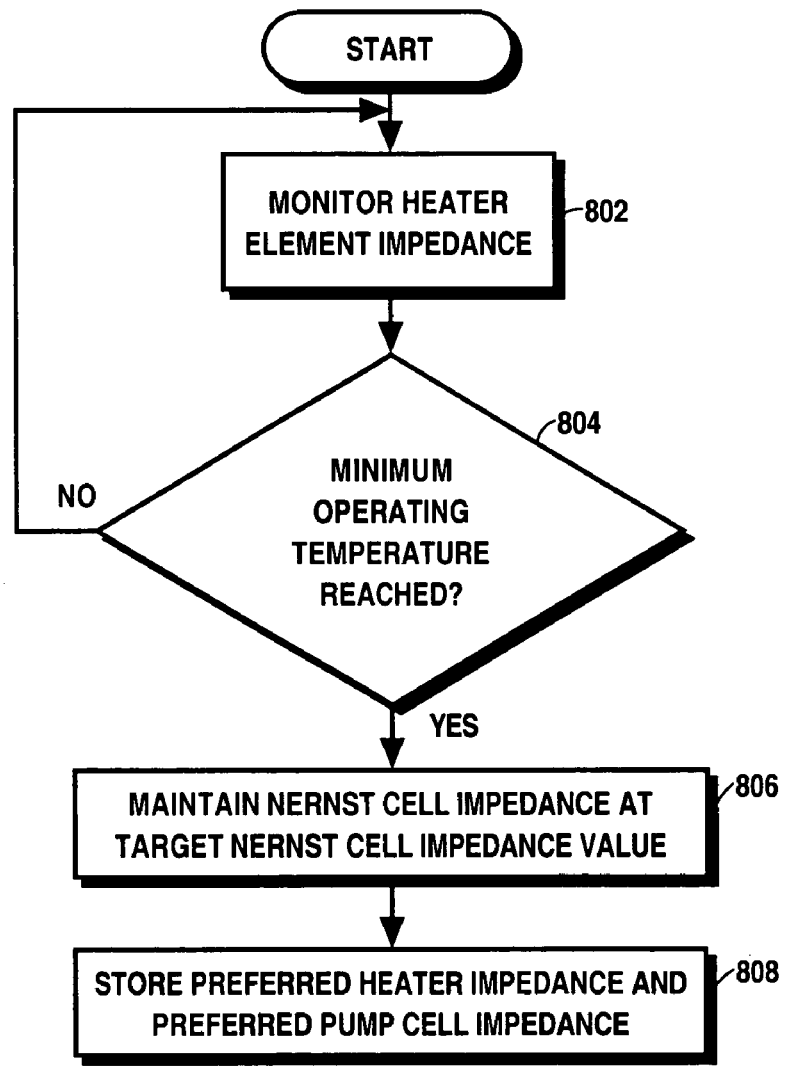
FIG. 8 is a flow chart of a method of calibrating the heater control unit in accordance with the exemplary embodiment of the invention.

FIG. 8 is flow chart of an exemplary method of calibrating the heater control unit 302. The method discussed with reference to FIG. 8, therefore, provides an exemplary method for performing step 606 of FIG. 6.

At step 802, the heater element 330 impedance is monitored as the temperature of the heater element 330 is increased. In the exemplary monitoring device described with reference to FIG. 3, the analog switch 316 is initially opened during the heater unit calibration procedure. In accordance with the appropriate heating timetable, power is applied to the heater element 330 to increase the temperature. The heater control unit 302 monitors the current and voltage across the heating element and determines the impedance of the heater element. Based on stored information relating the heater element impedance to the temperature of the heater element 330, the heater control unit 302 determines when the minimum operating temperature of the oxygen sensor cell 206 is reached. In response to a determination that the desired minimum operating temperature is reached, the heater control unit 302 presents a "high" enable signal at the "Ready" output. The AND gate (U3) 318 closes the analog switch 316 when the ENABLE signal goes "high".

At step 804 it is determined whether the minimum operating temperature has been reached. The procedure proceeds to step 806 when the minimum operating temperature is reached. Otherwise, the heater temperature continues to be monitored at step 802 with the analog switch 316 opened.

At step 806, the Nernst cell impedance is maintained at the target Nernst cell impedance. The heater control unit 302 is controlled such that the temperature is varied to maintain the Nernst cell impedance at the target value. The target Nernst cell impedance is a predetermined value that depends on the type and brand of the measuring cell (sensor) 202 and is provided by the sensor manufacturer. The Nernst cell impedance is held constant or nearly constant for a minimum time to allow fluctuations in temperatures and impedances to settle. An example of a suitable settling time is ten seconds.

As described above, the Nernst cell (206) impedance is monitored by passing the output voltage signal of the Nernst cell (206) through a high pass filter and amplifier (not shown).The resulting filtered and amplified signal is sampled at the comparator transition point. The peak-peak voltage, $U_{NPP}$, is calculated as the difference between the sample voltage at low-high and high-low transition in accordance with Equation 2.

At step 808, the preferred heater impedance and the preferred pump cell impedance are measured and stored. In the exemplary embodiment, the pump cell impedance is calculated based on Equation 1. As discussed above, the voltage at the pump cell 204 (output of $U_2$) is determined by Vcc, $R_{PUMP}$, the resistor $R_4$, and the back-EMF of the pump cell 204 when the oxygen measuring device 200 is in an oscillating mode. The output of the operational amplifier ($U_1$) 322 of the comparator 304 switches between 0V and Vcc. The heater control unit 302 samples the output of the operational amplifier ($U_2$) 308 before and after each transition of the output of the operational amplifier ($U_1$) 322. The absolute value of the difference between the voltage measured before and after each transition is $U_{DIFF}$. In some circumstances, the output of the operational amplifier ($U_2$) 322 is passed through a high pass filter (not shown) of sufficiently high cut-off frequency. The filter output is sampled immediately after the transition point and the absolute value of resulting output voltage is equal to $U_{DIFF}$.

Although various calibration factors and equations may be used depending on the particular implementation of the oxygen measuring device, the above equations are derived based on the following analysis and assumptions in the exemplary embodiment. Those skilled in the art will recognize the modifications based on the teachings herein.

The relationships between the various parameters are described below with reference to equations 5–26 where the following is assumed:

$Q_f$ is the required oxygen flow in and out of the measuring cell 202 to maintain the Nernst cell (206) at the transition point;

$Q_1$ is an oxygen flow value out of the Nernst cell (206) at the fixed constant current (Ip);

$Q_2$ is an oxygen flow value into the Nernst cell (206) at the fixed constant current (–Ip);

$t_1$ is the oxygen pump time ($Q_1$ flow) required to switch the Nernst cell (206) from 0.445V to 0.455V; and $t_2$ is the oxygen pump time ($Q_2$ flow) required to switch the Nernst cell (206) from 0.455V to 0.445V.

For the forgoing assumptions, therefore, the Nernst cell (206) voltage is 0.45V with an alternating current (AC) component of 10 mVpp. The resulting $Q_f$ is:

$$Q_f = (Q_1 * t_1 - Q_2 * t_2)/(t_1 + t_2) \quad (5)$$

The timing relationships can be expressed as $$PWM_{RATIO} = (t_1 - t_2)/(t_1 + t_2) \quad (6)$$

Using 1 and 2, equation 1 can be rewritten as:

$$Q_f = [(Q_1 + Q_2) * PWM_{RATIO} + Q_1 - Q_2]/2 \quad (7)$$

Pump flow ratio ($Q_{RAT}$) can be expressed as:

$$Q_{RAT} = (Q_1 - Q_2)/(Q_1 + Q_2) \quad (8)$$

At changing air pressure, $Q_1$ and $Q_2$ change approximately proportionally and, therefore, $Q_{RAT}$ stays nearly constant. The same holds true for temperature changes. Accordingly, $Q_{RAT}$ is independent of temperature.

In some circumstances, $Q_{RAT}$ may change when the sensor ages and, therefore, the sensor may need to be periodically calibrated to maintain optimal performance.

If $Q_1$ and $Q_2$ are known and are constants, the oxygen flow rate and Lambda, ($\lambda$) is determined from the timing relationship, $PWM_{RATIO}$, which is measured. $Q_1$ and $Q_2$ are constant if the pump current 208, temperature, exhaust pressure, barometric pressure and oxygen concentration in air are constant. In the exemplary embodiment, the pump current 208 and temperature are held constant through careful circuit design. For the analysis described herein, the atmospheric oxygen concentration is assumed to be constant at 20.9%. Barometric pressure effects are compensated through calibration. The effect of exhaust pressure tends to modify both, $Q_1$ and Q2 by an equal factor and also modifies the response time of the oxygen sensor cell 206 because more or less oxygen ions are present at the oxygen sensor cell 206 surface depending on pressure.

As described above, the oxygen monitoring device 200 measures oxygen flow by switching the pump current 208 between a constant positive and negative value. The absolute value for this constant pump current value is chosen such that it is greater than the absolute value of the pump current 208 required for free air.

The above equation is linear and can be determined with two known points. The time values $t_1$ and $t_2$ are measured by a crystal controlled microprocessor or timer circuit which allows the accurate determination of Lambda, ($\lambda$), once the two calibration points are known.

A stoichiometric exhaust mixture does not require any corrective oxygen flow and the steady state pump current 208 is, therefore, equal to zero. This condition is used to determine one of the calibration points, the stoichiometric pulse width ratio, $PWM_{ST}$.

As described above, a second calibration point is obtained by measuring the pulse width ratio when the measured gas is air. The measuring cell 202 is exposed to free air. If the measuring cell 202 is not installed in a vehicle, the measuring cell is placed in an area exposed to free air. If the measuring cell 202 is installed in a vehicle, the calibration for free air is performed when the vehicle has not been in operation for an adequate time and all the exhaust gases have dissipated or when the vehicle is in a cost-down mode. During the coast-down mode, the throttle on the engine is completely closed and engine speed is above a predetermined value. In this case, a typical ECU will not inject any fuel because no power output is required from the engine and further fuel can be saved. The pump cell 204 is then driven with a total flow value $Q_F$ that is high enough to pump all oxygen from the air in the measurement chamber.

From equations 5 through 8 follows:

$$PWM_{ST} = -Q_{RAT} \quad (9)$$

The lambda value, $\lambda$, calculated from exhaust oxygen concentration can be expressed as:

$$\lambda = \text{Air Oxygen content}/(\text{Air Oxygen content} - \text{Excess Oxygen}) \quad (10)$$

Note that the value Excess Oxygen in Equation 6 can have negative values if all oxygen is consumed but unburned or partially burned fuel is still present.

To examine the oxygen flow rate instead of volume, t is eliminated by division:

$$\lambda = Q_{f(AIR)}/(Q_{f(AIR)} - Q_f): \quad (11)$$

applying equations 7,8,9, and 11:

$$\lambda = (PWM_{AIR} - PWM_{ST})/(PWM_{AIR} - PWM_{RATIO}) \quad (12)$$

As described above, a second free air PWM ratio ($PWM'_{AIR}$) is measured by switching the pump cell 204 between $Q_1$ and no current ($Q_2 = 0$) during free air calibration.

$PWM_{ST}$ is calculated during calibration from $PWM_{AIR}$ and $PWM'_{AIR}$ according to the following formulas:

From equation 7, $$2*Q_f = (Q_1 + Q_2)*PWM_{AIR} + Q_1 - Q_2 \quad (13)$$

$$2*Q_f = Q_1 * PWM'_{AIR} + Q_1 \quad (14)$$

Where $PWM'_{AIR}$ is measured when switching between $Q_1$ and no current instead of $Q_1$ and $Q_2$.

$$P = PWM_{AIR} - PWM_{ST}. \quad (15)$$

From equations 13 and 14:

$$P = (1 + PWM'_{AIR})*(1 - PWM_{AIR})/(1 - PWM'_{AIR}) \quad (16)$$

$$PWM_{ST} = PWM_{AIR} - P \quad (17)$$

Applying equation (12):

$$\lambda = P/(PWM_{AIR} - PWM_{RATIO}) \quad (18)$$

As explained above, $PWM_{AIR}$ is measured by exposing the sensor to free air at the appropriate operating temperature and, in some circumstances, frequency information is used for determining compensation factors. The following analysis demonstrates the relationship between frequency and other parameters.

Returning to equation 8, if $Q_1 = Q_2$, $Q_{RAT}$ (and therefore $PWM_{ST}$) becomes zero. The actual sampling frequency is dependent on the full flow ratio, $Q_F$.

Equation 8 then changes to:

$$Q_f = Q_F * PWM_{RATIO}. \quad (19)$$

Equation 12 becomes $$\lambda = PWM_{AIR}/(PWM_{AIR} - PWM_{RATIO}) \quad (20)$$

$Q_F$ is a function of the pump current 208, Ip, and, therefore, $Q_F = f(Ip)$. If $Q_F$ for a constant Ip changes because of exhaust pressure changes, the measured $PWM_{RATIO}$ becomes $PWM'_{RATIO}$ for the same corrective flow, $Q_f$.

With exhaust gas pressure or temperature changes $Q_1$ and $Q_2$ change by a factor K in a first approximation.

Equation 8 then becomes:

$$Q_f = K*[(Q_1 + Q_2)*PWM'_{AIR} + Q_1 - Q_2]/2 \quad (21)$$

where $$Q_1*t_1 = K*Q_1*t_1' \quad (22)$$

$$Q_2*t_2 = K*Q_2*t_2' \quad (23)$$

The measurement frequency f is determined by:

$$f = 1/(t_1 + t_2) \quad (24)$$

$$f' = 1/(t_1' + t_2') \quad (25)$$

From equations 20, 21, 22 and 23 follows:

$$K = f'/f \quad (26)$$

Because f is constant when all other environmental conditions are constant, this calculation can be used to correct for temperature and/or pressure changes. Equation 8 then becomes:

$$\lambda = (PWM_{AIR} - PWM_{ST})/(PWM_{AIR} - (1-K) \\ *PWM_{ST} - K*PWM'_{RATIO}) \quad (27)$$

and equation 18 becomes:

$$\lambda = PWM_{AIR}/(PWM_{AIR} - K*PWM'_{RATIO}) \quad (28)$$

These equations, therefore, allow the application of a pressure compensation factor, K to compensate for pressure or temperature changes. Under extreme circumstances, $Q_1$ and $Q_2$ do not change equally by the same factor K. In some situations, therefore, the normalized frequency deviation $f'/f$ is used as an index into an experimentally derived lookup table to extract the accurate deviation factor K':

$$K' = \text{func } (f'/f). \quad (29)$$

The calculated Lambda value can thus be corrected for exhaust pressure changes without the use of separate sensors to measure exhaust pressure once a normalized frequency/lambda table is experimentally determined for a given sensor type.

Conventional commercially available packaged measuring cells 202 often have temperature dependent parasitic resistances to the virtual ground of the pump cell 204 and Nernst cell (206). This parasitic resistance must be addressed through software or circuitry in order to apply pressure compensation methods described above with many commercially available measuring cells 202.

The forgoing equations and analysis may be applied to other implementations of the invention in ways other than described above and the teachings described herein may be applied to a variety of formats, implementations and configurations. As explained above, the hardware and software may be modified to accommodate a variety of factors. For example, the analog switch 316 can be eliminated where the operational amplifier ($U_2$) 308 provides a tri-state output. Also, the analog switch 316 can be connected within the oxygen measuring device 200 before the inverting resistor ($R_4$) 310 instead of connecting to the output of the operational amplifier ($U_2$) 308. The operational amplifier ($U_2$) 308 may also provide a tri-state output. In addition, the heater controlling unit 302 may be integrated as part of the computing device 218.

Further, the Zener diode 314 may be replaced with a digital to analog (D/A) converter or a potentiometer in some circumstances. The references voltage $U_{REF}$ could thereby be set such that the pulse width ratio at the stoichiometric ratio, $PWM_{ST}$ is exactly zero. In such a circumstance, the equation used to calculate $\lambda$ is:

$$\lambda = PWM_{AIR}/(PWM_{AIR} - K*PWM') \quad (30)$$

In some circumstances, frequency information is analyzed to provide other useful information or data in accordance with the analysis above. For example, because the response time of a measuring cell 202 changes with aging, the oscillating frequency is used directly as a measurement to determine the need for replacement. When a lower threshold frequency is reached, the computing device 218 may provide a warning that the sensor should be replaced. The frequency analysis is preferably performed when the free-air value is recalibrated because the environmental conditions are comparable (f' and f in equation 27 are equal) and the frequency change is due to aging of the sensor.

Figure 9:
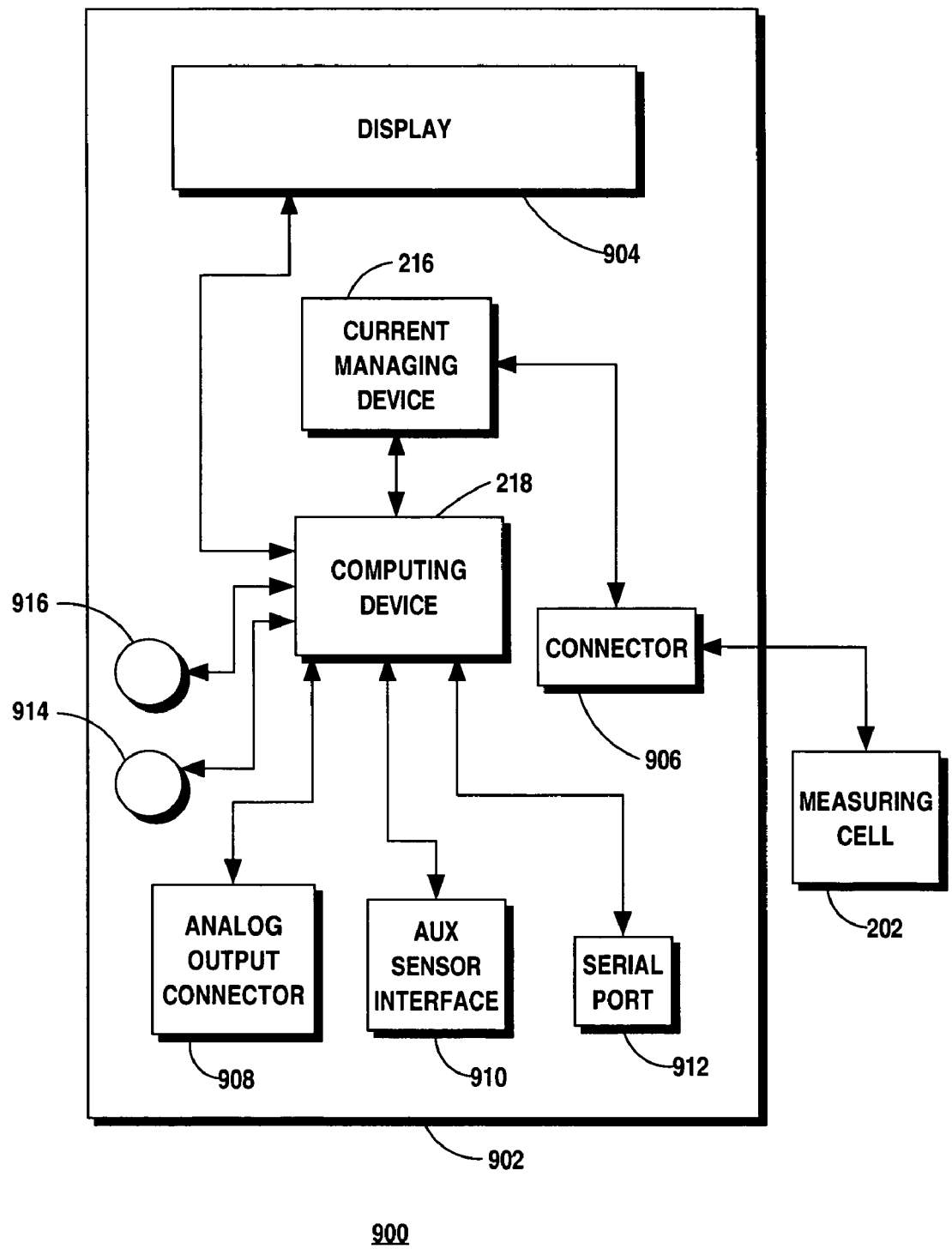
FIG. 9 is a block diagram of a hand-held diagnostic device suitable for embodying the oxygen measuring device.

FIG. 9 is a block diagram of an exemplary hand-held diagnostic device suitable for embodying the oxygen measuring device 200. As mentioned above, the oxygen measuring device 200 may be implemented as any of several configuration and devices. The oxygen measuring device 200, for example, may be integrated as an OEM device in a vehicle fuel system. Further, the oxygen measuring device 200 may be part of an in-vehicle aftermarket fueling system or diagnostic system. Other devices and uses will be readily apparent to those skilled in the art based on the teachings herein.

The exemplary hand-held diagnostic device 900 includes a housing 902, a display 904, connectors 906–912, and buttons (or other type of switches) 912, 914 that provide interfaces to the computing device 218 and the current managing device 216. The display allows the user to view information regarding the status to the hand-held diagnostic device 900. In the exemplary hand held device 900, the connectors 906–912 include a serial port 912 for connecting to an external computer analog output connector 908 for supplying an analog signal corresponding to the measured $\lambda$, an auxiliary sensor interface 919, and a sensor connector 906. Other connectors such as a power connector for receiving DC supply power, for example, are also included in some circumstances. A calibrate button 908 connected to the computing device 218 provides a user interface for initiating the calibration procedure. A record button 914 provides a user interface for initiating a record procedure that allows several seconds of data to be stored in memory. An example of another button or switch that may be used includes an on-off switch (not shown). The buttons and connectors are connected to the computing device 218 and other circuitry and provide interfaces between the user, the measuring device 200, the measuring cell 202 and other external equipment.

Therefore, the system, apparatus and method for measuring the oxygen concentration of gas provides a cost effective, efficient and accurate way to monitor a gas having several advantages over conventional systems. The techniques described herein provide a simplified design since no analog to digital (A/D) conversion is required for a oxygen concentration ($\lambda$) measurement. Further, no calibration resistor is required in the measuring cell sensor to compensate for sensor tolerances which results in simplified production and lower production costs. Wide tolerances of the measuring cell 202 itself are acceptable, resulting in higher possible production yield. Because no precision resistors or other precision parts are required, circuit cost is minimized. The oxygen monitoring device 200 self-compensates for pressure and temperature variations. The measurement process is converted to the time-domain, instead of an analog current/voltage domain. By using standard crystal time bases, as is typical in digital designs, temperature and age-related drifts are eliminated because crystal time bases have tolerances of $<10^{-6}$ compared to $<10^{-2}$ for typical resistors. Measurement results are linear to 1/Lambda and independent of the Ip/Lambda curve of the sensor. Calibration is convenient and uses only air as a reference gas.

Clearly, other embodiments and modifications of this invention will occur readily to those of ordinary skill in the art in view of these teachings. Therefore, this invention is to be limited only by following claims, which include all such embodiments, equivalents, and modifications when viewed in conjunction with the above specification and accompanying drawings.

What is claimed is:

1. An apparatus comprising:
an oxygen sensor cell for providing an output signal in accordance with an oxygen concentration of a gas within a measuring cell;
a pump cell for adjusting an oxygen ion flow between the measuring cell and ambient air in accordance with a pump current flowing through the pump cell; and
a current managing unit for varying the pump current between a first constant current and a second constant current in accordance with the output signal.

2. An apparatus in accordance with claim 1, further comprising:
a computing device configured to determine an oxygen concentration of the gas based on a pulse width ratio of a square wave of the pump current.

3. An apparatus in accordance with claim 2, wherein the current managing unit is configured to vary the pump current by maintaining the first constant current in a first direction until a first output signal threshold is detected and maintaining the second constant current in a second direction until a second output signal threshold is detected.

4. An apparatus in accordance with claim 3, wherein the current managing unit comprises:
an analog comparator circuit configured to provide a comparator output signal based on the output of the oxygen sensor cell, the comparator output signal indicating when the first output signal threshold is reached and when the second output signal threshold is reached; and
an inverting amplifier circuit connected between the analog comparator circuit and the oxygen sensor cell, the inverting amplifier circuit configured to change the direction of the pump current in response to the comparator output signal.

5. An apparatus in accordance with claim 4, wherein the computing device is configured to determine the pulse width ratio by:
measuring a first time period corresponding to the first constant current;
measuring a second time period corresponding to the second constant current;
determining the pulse width ratio based on the first time period and the second time period; and
determining the oxygen concentration of the gas by comparing the pulse width ratio to a pulse width ratio function for the measuring cell.

6. An apparatus in accordance with claim 5, wherein the computing device is connected to the comparator circuit, the computing device configured to measure the first time period and the second time period based on the comparator output signal.

7. An apparatus in accordance with claim 6, wherein the computing device is configured to determine at least some values of the pulse width ratio function by determining a pulse width ratio for free air, $PWM_{AIR}$, when the measuring cell is exposed to free air and the first constant current is a positive pump current and the second constant current is a negative pump current.

8. An apparatus in accordance with claim 7, wherein the computing device is further configured to determine at least some of the values of the pulse width ratio function by determining a stoichiometric pulse width ratio, $PWM_{ST}$, based on a pulse width ratio for free air when the first constant current is a positive pump current and the second constant current is zero.

9. An apparatus in accordance with claim 8, wherein the computing device establishes the second pump current by opening an analog switch connected between the inverting amplifier circuit and the pump cell in accordance with a negative current cycle.

10. An apparatus in accordance with claim 9, wherein the oxygen sensor cell is a Nernst cell.

11. An apparatus in accordance with claim 2, wherein the computing device is configured to determine the oxygen concentration based on a frequency of the square wave.

12. An apparatus in accordance with claim 11, wherein the computing device is configured to apply a pressure compensation factor based on the frequency to determine the oxygen concentration.

13. An apparatus in accordance with claim 2, further comprising:
a user interface connected to the computing device.

14. An apparatus in accordance with claim 2, wherein the apparatus is configured to connect to a fuel system for a combustion engine.

15. An apparatus configured to connect to a measuring cell, the apparatus comprising:
a current managing unit configured to receive an output signal based on an oxygen concentration of a gas within the measuring cell and to adjust an oxygen ion flow between the measuring cell and ambient air by varying, in accordance with the output signal, a pump current flowing through a pump cell of the measuring cell between a first constant current and a second constant current.

16. An apparatus in accordance with claim 15, wherein the output signal is produced by an oxygen sensor cell of the measuring cell.

17. An apparatus in accordance with claim 15, further comprising:
a computing device configured to determine an oxygen concentration of the gas based on a pulse width ratio of a square wave of the pump current.

18. An apparatus in accordance with claim 17, further comprising:
a user interface connected to the computing device.

19. An apparatus in accordance with claim 15, wherein the apparatus is configured to connect to a fuel system for a combustion engine.

20. An apparatus in accordance with claim 17, wherein the current managing unit is configured to vary the pump current by maintaining the first constant current in a first direction until a first output signal threshold is detected and maintaining the second constant current in a second direction until a second output signal threshold is detected.

21. An apparatus in accordance with claim 20, wherein the current managing unit comprises:
an analog comparator circuit configured to provide a comparator output signal based on the output of the measuring cell, the comparator output signal indicating when the first output signal threshold is reached and when the second output signal threshold is reached; and
an inverting amplifier circuit connected between the analog comparator circuit and the measuring cell, the inverting amplifier circuit configured to change the direction of the pump current in response to the comparator output signal.

22. An apparatus in accordance with claim 21, wherein the computing device is configured to determine the pulse width ratio by:
measuring a first time period corresponding to the first constant current;
measuring a second time period corresponding to the second constant current;
determining the pulse width ratio based on the first time period and the second time period; and
determining the oxygen concentration of the gas by comparing the pulse width ratio to a pulse width ratio function for the measuring cell.

23. An apparatus in accordance with claim 22, wherein the computing device is connected to the comparator circuit, the computing device configured to measure the first time period and the second time period based on the comparator output signal.

24. An apparatus in accordance with claim 23, wherein the computing device is configured to determine at least some values of the pulse width ratio function by determining a pulse width ratio for free air, $PWM_{AIR}$, when the measuring cell is exposed to free air and the first constant current is a positive pump current and the second constant current is a negative pump current.

25. An apparatus in accordance with claim 24, wherein the computing device is further configured to determine at least some of the values of the pulse width ratio function by determining a stoichiometric pulse width ratio, $PWM_{ST}$, based on a pulse width ratio for free air when the first constant current is a positive pump current and the second constant current is zero.

26. An apparatus in accordance with claim 25, wherein the computing device establishes the second pump current by opening an analog switch connected between the inverting amplifier circuit and the pump cell in accordance with a negative current cycle.

27. An apparatus in accordance with claim 26, wherein the oxygen sensor cell is a Nernst cell.

28. An apparatus in accordance with claim 17, wherein the computing device is configured to determine the oxygen concentration based on a frequency of the square wave.

29. An apparatus in accordance with claim 28, wherein the computing device is configured to apply a pressure compensation factor based on the frequency to determine the oxygen concentration.

30. An apparatus in accordance with claim 22, wherein the computing device is further configured to perform a calibration procedure by determining at least some factors of the pulse width function.

31. An apparatus in accordance with claim 30, wherein the computing device is configured to determine at least some of the factors by determining a corresponding oxygen ion flow for a constant pump current when the measuring cell is exposed to a known gas with a known oxygen concentration.

32. An apparatus in accordance with claim 31, wherein the computing device is configured to determine the corresponding oxygen ion flow by determining a relationship between a Lambda coefficient of the oxygen sensor cell and the pulse width ratio.

33. An apparatus in accordance with claim 32, wherein the computing device is configured to determine the relationship between the Lambda coefficient of the oxygen sensor cell and the pulse width ratio by determining at least two points on a line representing the relationship between Lambda and the pulse width ratio.

34. An apparatus in accordance with claim 33, wherein the computing device is configured to determine at least two points on the line representing the relationship between Lambda and the pulse width ratio by observing a calibration pulse width ratio occurring when the current managing unit directs the pump current in the positive direction until an upper threshold is reached and directs no pump current until a lower threshold is reached.

35. An apparatus in accordance with claim 30, wherein the computing device is configured to perform the calibration procedure by determining a positive corresponding oxygen ion flow for a positive constant pump current and determining a negative corresponding oxygen ion flow for the a negative constant pump current when the measuring cell is exposed to a first known gas with a known oxygen concentration.

36. An apparatus comprising:
a sensor connector configured to connect to a measuring cell and receive an output signal based on an oxygen concentration of a gas within a measuring cell, the output signal produced by an oxygen sensor cell of the measuring cell; and
a current managing unit configured to adjust an oxygen ion flow between the measuring cell and ambient air by varying, in accordance with the output signal, a pump current flowing through a pump cell of the measuring cell between a first constant current and a second constant current.

37. An apparatus in accordance with claim 36, wherein the current managing unit is configured to vary the pump current by maintaining the first constant current in a first direction until the output signal reaches a first output signal threshold and maintaining the second constant current in a second direction until the output signal reaches a second output signal threshold, the apparatus further comprising:

a computing device configured to determine an oxygen concentration of the gas based on a pulse width ratio of a square wave of the pump current resulting from the varying of the pump current.

38. An apparatus in accordance with claim 37, wherein the current managing unit comprises:

an analog comparator circuit configured to provide a comparator output signal based on the output of the oxygen sensor cell, the comparator output signal indicating when the first output signal threshold is reached and when the second output signal threshold is reached; and an inverting amplifier circuit connected between the analog comparator circuit and the oxygen sensor cell, the inverting amplifier circuit configured to change the direction of the pump current in response to the comparator output signal.

39. An apparatus configured to connect to a measuring cell, the apparatus comprising:

a current managing unit configured to receive an output signal based on an oxygen concentration of a gas within the measuring cell and to adjust an oxygen ion flow between the measuring cell and ambient air by varying, in accordance with the output signal, a pump current flowing through a pump cell of the measuring cell between a first constant current and a second constant current, the output signal produced by an oxygen sensor cell of the measuring cell; and a computing device configured to determine an oxygen concentration of the gas based on a pulse width ratio of a square wave of the pump current.

40. An apparatus in accordance with claim 39, wherein the current managing unit is configured to vary the pump current by maintaining the first constant current in a first direction until a first output signal threshold is detected and maintaining the second constant current in a second direction until a second output signal threshold is detected and wherein the computing device is configured to determine the pulse width ratio by:

measuring a first time period corresponding to the first constant current;

measuring a second time period corresponding to the second constant current;

determining the pulse width ratio based on the first time period and the second time period; and determining the oxygen concentration of the gas by comparing the pulse width ratio to a pulse width ratio function for the measuring cell.

41. An apparatus configured to connect to a measuring cell and to determine an oxygen concentration of a gas within the measuring cell, the apparatus comprising:

a current managing unit configured to vary a pump current flowing through a pump cell of the measuring cell by maintaining a first constant pump current in a first direction until an output signal of an oxygen sensor cell of the measuring cell reaches a first output signal threshold and maintaining a second constant current in a second direction until the output signal reaches a second output signal threshold; and a computing device configured to:

measure a first time period corresponding to the first constant pump current;

measure a second time period corresponding to the second constant pump current;

determine a pulse width ratio of a square wave of the pump current based on the first time period and the second time period; and determine the oxygen concentration of the gas by comparing the pulse width ratio to a pulse width ratio function for the measuring cell.

\* \* \* \* \*